(12) United States Patent
Colla et al.

(10) Patent No.: US 8,303,897 B2
(45) Date of Patent: Nov. 6, 2012

(54) CAPACITIVE SENSOR FOR ORGANIC CHEMICALS COMPRISING AN ELASTOMER AND HIGH DIELECTRIC MATERIALS WITH TITANATE

(76) Inventors: Jeannine O. Colla, Grafton, WI (US); Paul E. Thoma, Cedarburg, WI (US)

( * ) Notice: Subject to any disclaimer, the term of this patent is extended or adjusted under 35 U.S.C. 154(b) by 0 days.

(21) Appl. No.: 13/036,886

(22) Filed: Feb. 28, 2011

(65) Prior Publication Data
US 2012/0220041 A1   Aug. 30, 2012

(51) Int. Cl.
*G01N 30/96* (2006.01)

(52) U.S. Cl. .............. 422/88; 422/82.01; 422/82.02; 422/83; 422/90

(58) Field of Classification Search .............. None
See application file for complete search history.

(56) References Cited

U.S. PATENT DOCUMENTS

| | | |
|---|---|---|
| 3,802,268 A | 4/1974 | Thoma |
| 3,814,998 A | 6/1974 | Thoma et al. |
| 4,965,698 A | 10/1990 | Thoma et al. |
| 5,150,603 A | 9/1992 | Boenning et al. |
| 5,177,662 A | 1/1993 | Thoma |
| 5,408,381 A | 4/1995 | Thoma et al. |
| 5,417,100 A | 5/1995 | Miller et al. |
| 5,512,882 A * | 4/1996 | Stetter et al. ............ 340/632 |
| 5,522,980 A | 6/1996 | Hobbs et al. |
| 5,538,620 A | 7/1996 | Nikolskaja |
| 5,644,069 A | 7/1997 | Liu et al. |
| 6,013,201 A | 1/2000 | Hayashida et al. |
| 6,433,694 B1 | 8/2002 | Dolan et al. |
| 6,868,350 B2 | 3/2005 | Zimmermann et al. |
| 7,138,090 B2 | 11/2006 | Blok |
| 7,421,883 B2 | 9/2008 | Khadkikar et al. |
| 7,708,947 B2 | 5/2010 | West et al. |
| 7,799,276 B2 | 9/2010 | Hartmann-Thompson |
| 7,834,527 B2 * | 11/2010 | Alvarez Icaza Rivera et al. ............... 310/344 |

(Continued)

FOREIGN PATENT DOCUMENTS
JP       09031244 A   *   2/1997

OTHER PUBLICATIONS

Khastgir and Adachi, "Piezoelectric and Dielectric Properties of Siloxane Elastomers Filled with Bariumtitanate", Journal of Polymer Science: Part B: Polymer Physics, 1999, v. 37, pp. 3065-3070.*

(Continued)

*Primary Examiner* — Yelena G Gakh
(74) *Attorney, Agent, or Firm* — Andrus, Sceales, Starke & Sawall, LLP

(57) ABSTRACT

An organic chemical sensor includes a dielectric core that comprises an elastomer and a high dielectric constant material. The elastomer absorbs an organic chemical to be sensed. An electrically conductive layer is secured to a first side of the dielectric core. A permeable conductive layer is secured to a second side of the dielectric core. The permeable conductive layer is electrically conductive and permeable to the organic chemical to be sensed. The absorption of the organic chemical to be sensed by the elastomeric layer causes a decrease in the capacitance between the electrically conductive layer and the permeable conductive layer.

22 Claims, 6 Drawing Sheets

U.S. PATENT DOCUMENTS

| | | | |
|---|---|---|---|
| 2003/0230725 A1 | 12/2003 | Wong | |
| 2008/0206105 A1* | 8/2008 | Centanni | 422/82.01 |
| 2009/0273356 A1 | 11/2009 | Pampin et al. | |
| 2009/0301875 A1 | 12/2009 | Wu et al. | |
| 2009/0302714 A1 | 12/2009 | Kim | |
| 2010/0133120 A1 | 6/2010 | Varney et al. | |
| 2010/0201383 A1 | 8/2010 | Morita et al. | |
| 2010/0225337 A1 | 9/2010 | Zamborini et al. | |

OTHER PUBLICATIONS

Patel et al., "Chemicapacitive microsensors for volatile organic compound detection", Sensors and Actuators, 2003, v. 96, pp. 541-553.*

Kummer, Ph.D. Thesis "Tuning Sensitivity and Discrimination Performance of CMOS Capacitive Chemical Microsensor Systems", 2004, Switzerland, Zurich, pp. 1-152.*

* cited by examiner

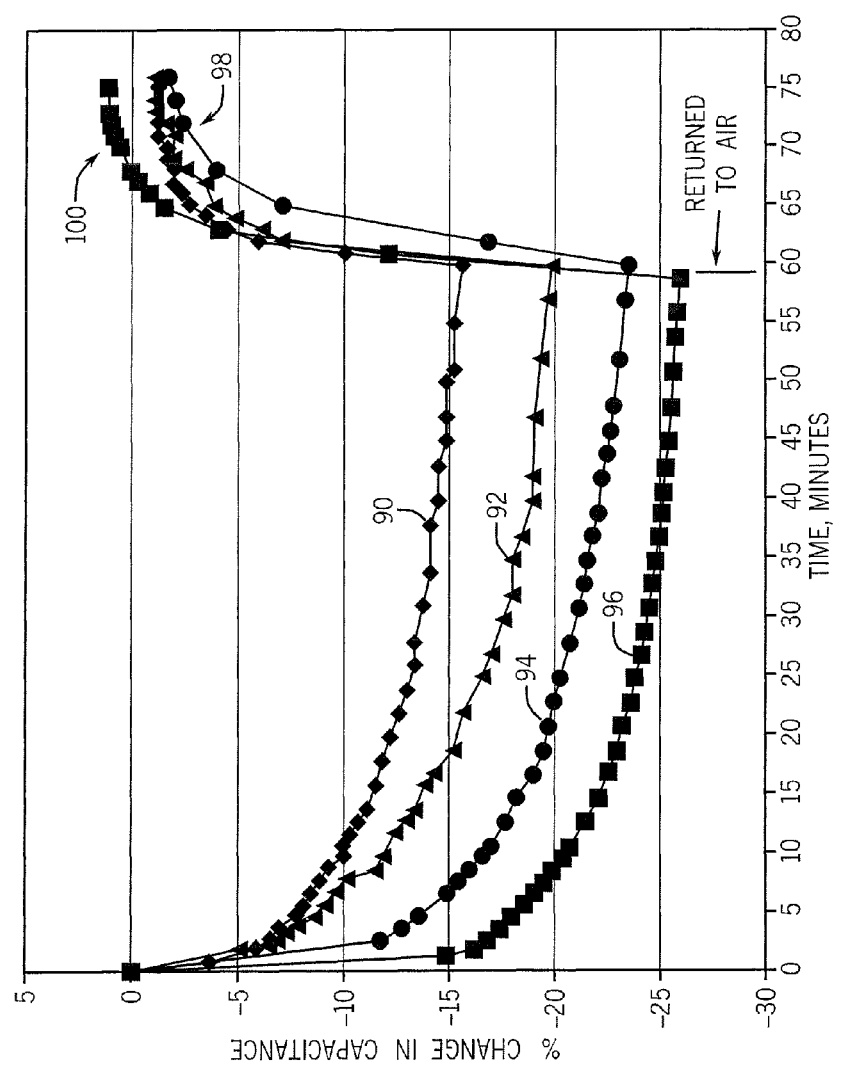

CAPACITIVE SENSOR FOR ORGANIC CHEMICALS COMPRISING AN ELASTOMER AND HIGH DIELECTRIC MATERIALS WITH TITANATE

BACKGROUND

The present disclosure is related to the field of sensors. More specifically, the present disclosure is related to electronic sensors for organic chemicals. Organic chemicals are a broad class of compounds that contain carbon. Common examples of organic chemicals are hydrocarbons or other petroleum based compounds that are commonly used as fuel sources. Electronic sensors for these compounds often measure a change in electrical resistance across a sensor after exposure to the chemicals.

Capacitance type sensors have been used as water vapor sensors and fluid pressure sensors to detect either relative humidity in an air environment or fluid pressure in pneumatic control systems.

Due to ongoing changes and increases in environmental regulations, the detection and monitoring of concentrations of organic chemicals is desired with greater accuracy and sensitivity than is achieved with current devices and methods.

BRIEF DISCLOSURE

An organic chemical sensor includes a dielectric core. The dielectric core includes an elastomer and a high dielectric constant material. The dielectric core further has a first side and a second side. The elastomer absorbs an organic chemical that is to be sensed. An electrically conductive layer is secured to the first side of the dielectric core. A permeable conductive layer is secured to the second side of the dielectric core. The permeable conductive layer is electrically conductive and permeable to the organic chemical to be sensed. Absorption of the organic chemical to be sensed by the elastomeric layer causes a decrease in the capacitance between the electrically conductive layer and the permeable conductive layer.

A method of sensing a concentration of an organic chemical includes providing an organic chemical sensor in an environment to be tested. The organic chemical sensor includes an electrically conductive layer. A dielectric core is secured to the electrically conductive layer. The dielectric core includes an elastomeric layer that absorbs the organic chemical and further includes a high dielectric constant material. A permeable conductive layer is secured to the dielectric core. The permeable conductive layer is permeable to the organic chemical and is electrically conductive. A capacitance between the electrically conductive layer and the permeable conductive layer is measured with a controller. The controller is electrically connected to the electrically conductive layer and the permeable conductive layer. The organic chemical sensor is exposed to an unknown quantity of the organic chemical. A decrease in the capacitance between the electrically conductive layer and the permeable conductive layer is measured with the controller. The controller derives a concentration of the organic chemical from the measured decrease in the capacitance between the electrically conductive layer and the permeable conductive layer.

An organic chemical sensing system includes a dielectric core, an electrically conductive layer, and a permeable conductive layer. The dielectric core includes an elastomeric layer with a high dielectric constant material. The elastomeric layer has an elongated first surface and an elongated second surface. The elastomeric layer absorbs an organic chemical to be sensed and absorption of the organic chemical to be sensed by the elastomeric layer decreases a dielectric constant of the dielectric core and increases a volume of the elastomeric layer. The electrically conductive layer is secured to the elongated first surface of the elastomeric layer. The electrically conductive layer fixes the area of the elongated first surface and the elongated second surface of the elastomeric layer. The permeable conductive layer is secured to the elongated second side of the elastomeric layer. The permeable conductive layer is electrically conductive and permeable to the organic chemical to be sensed. Absorption of the organic chemical to be sensed by the elastomeric layer causes a decrease in the capacitance between the electrically conductive layer and the permeable conductive layer.

BRIEF DESCRIPTION OF THE DRAWINGS

FIG. 10 is a graph that presents the percentage of change in capacitances detected by embodiments of the organic chemical sensor with varying high dielectric constant material concentrations.

DETAILED DISCLOSURE

FIGS. 1-8 all depict exemplary embodiments of an organic chemical sensor as disclosed in further detail herein. The disclosed organic chemical sensors change in capacitance when exposed to the organic chemical to be sensed. As disclosed above, hydrocarbons or petroleum products are examples of organic chemicals. However, other types of organic chemicals such as volatile organic compounds (VOC) and others would be recognized by one of ordinary skill in the art, may similarly be sensed by embodiments of the organic chemical sensor as disclosed herein.

The disclosed organic chemical sensor measures a change in capacitance across the sensor when the sensor is exposed to an organic chemical vapor. Capacitance is represented by the equation:

$$C = \frac{K \times \varepsilon_0 \times A}{D} \quad (1)$$

In the above equation, C represents capacitance. K is the dielectric constant of the material between electrically conductive layers. $\varepsilon_0$ is the electric constant ($\varepsilon_0 = 8.854 \times 10^{-12}$ F/m$^{-1}$). A is the area of overlap between the two electrically conductive layers. D is the distance between the electrically conductive layers. From equation (1) it can be seen that capacitance increases with increases in area of the sensor and decreases with greater distances between the electrically conductive layers. The capacitance is further highly dependent upon the dielectric constant of the material between the electrically conductive layers.

Embodiments of the organic chemical sensors as disclosed herein seek to maximize these characteristics of capacitance to improve sensor sensitivity.

Figure 1:
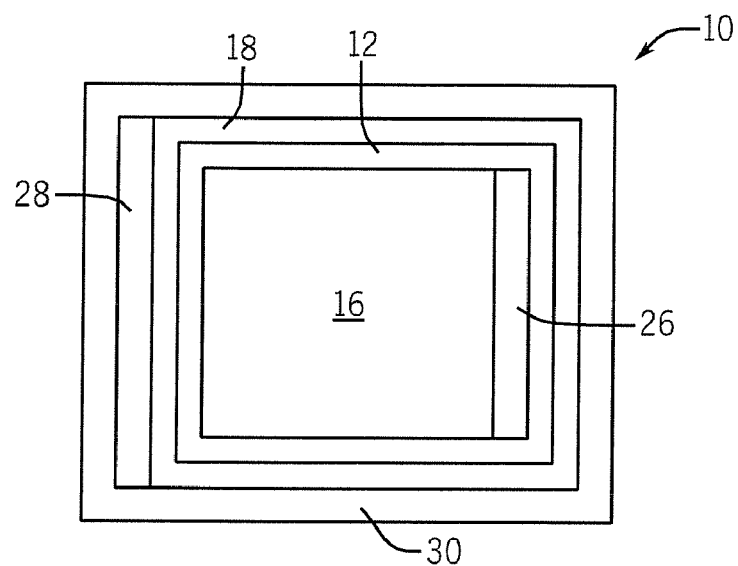
FIG. 1 is a top view of an embodiment of an organic chemical sensor.

FIG. 1 depicts an embodiment of an organic chemical sensor 10. The organic chemical sensor 10 includes dielectric core 12. In an embodiment, the dielectric core 12 is an elastomer constructed of a polymer with the characteristic of absorbing vapors of an organic chemical to be sensed. In a merely exemplary manner, the following description will use gasoline as the organic chemical to be sensed; however, it will be recognized by one of ordinary skill in the art that embodiments of the organic chemical sensor as disclosed herein can be constructed to detect concentrations of any of a variety of organic chemical vapors. Exemplarily, the elastomer is constructed of a silicone, a polyurethane, or an ethylene propylene rubber. In further embodiments, the elastomer has a hardness of less than 80 on the Durometer D scale and less than 95 on the Durometer A scale. Exemplarily, Momentive RTV 615 silicone has a hardness of 44 on the Durometer A scale after curing. Typical elastomers used have a relatively low dielectric constant (e.g. silicone 2.7 and polyurethane 3.5). These dielectric constants are similar to that observed for gasoline (2.0). Therefore, the absorption of gasoline by the elastomeric layer will result in minimal change to the dielectric constant of these dielectric cores.

A high dielectric constant material 14 is included in the dielectric core 12. In an embodiment, the high dielectric constant material is added to the elastomer to effectively increase the dielectric constant of the dielectric core 12. Exemplary materials that may be used as the high dielectric constant material 14 are barium titanate (dielectric constant 150-10,000), strontium titanate (dielectric constant 310), or barium strontium titanate (dielectric constant 500); however, it will be recognized by one of ordinary skill in the art that alternative high dielectric constant materials may be used in an alternative embodiment. In embodiments, the high dielectric constant material 14 has a dielectric constant greater than 100 and alternative embodiments have a dielectric constant greater than 1000. In still further embodiments, the high dielectric constant material 14 is selected to have a dielectric constant greater than 1000 times or more than the dielectric constant of the elastomer of the elastomeric layer.

Embodiments of the organic chemical sensor 10 form the elastomer into an elastomeric layer using methods as disclosed herein, although a person of ordinary skill in the art will recognize alternative suitable manufacturing processes.

In one embodiment, the elastomeric layer is constructed with a silicone elastomer that contains 75% by weight barium titanate according to the following: 92.34 grams barium titanate powder, 35.0 grams methyl ethyl ketone, 27.54 grams RTV 615 part A silicone (available from Momentive Performance Materials, Inc.), and 3.24 grams RTV 615 part B silicone (available from Momentive Performance Materials, Inc.). The elastomeric solution is prepared by mixing the barium titanate powder and methyl ethyl ketone. After the barium titanate and methyl ethyl ketone solution is thoroughly mixed, the part A silicone is mixed into the solution. The part B silicone is added and the final solution is mixed again. After application of the elastomer solution, as will be described in further detail herein, the methyl ethyl ketone is allowed to evaporate and the elastomer is cured by heating to a temperature between 150° F. and 250° F. for several hours. It is understood that this is merely an exemplary description of an elastomeric layer to be used in an embodiment of the organic chemical sensor as disclosed herein, and a person of ordinary skill in the art will recognize other means for manufacture of a suitable elastomeric layer.

The organic chemical sensor 10 further includes a permeable conductive layer 16. The permeable conductive layer 16 exhibits two properties. The first property is that the permeable conductive layer 16 is permeable to the organic chemical to be sensed. The second property is that the permeable conductive layer 16 is electrically conductive.

The permeable conductive layer 16 can be permeable to the organic chemical to be sensed in a variety of ways. In one embodiment, the permeable conductive layer 16 is a metal screen. Exemplarily, this screen is a 250-325 mesh phosphor bronze screen. In this embodiment, when the actual mesh screen is selected, the screen is selected such that the molecules of the organic chemical to be sensed, such as gasoline, are able to pass through the mesh with ease.

In an alternative embodiment, the permeable conductive layer 16 is constructed from a similar base elastomer as the elastomeric layer. By selecting the same base elastomer, the absorptive properties for the organic chemical to be sensed are similar in the permeable conductive layer 16 and in the elastomeric layer.

The second property of the permeable conductive layer 16, that of electrical conductivity, is either provided as a characteristic of the material, such as copper, bronze, silver, or gold of the mesh screen. Alternatively, if the elastomeric base is used as the permeable conductive layer, the elastomer can be loaded with a sufficient amount of electrically conductive particles in order to make the permeable conductive layer 16 electrically conductive. In one embodiment, the conductive particles added to the permeable conductive layer 16 are electrically conductive chaining type carbon particles exemplarily available from Cabot Corp. as Vulcan XC-72R. Alternatively, or in addition to the carbon particles, metal powder or flake, such as silver flake, can be further added to the permeable conductive layer 16 to increase the electrical conductive property of the permeable conductive layer 16. It has been found that metal particles of sizes between 2-10 microns have produced satisfactory results; however, a person of ordinary skill in the art would recognize alternatives that fall within the scope of the present disclosure.

In an exemplary embodiment of the construction of the permeable conductive layer 16, the permeable conductive layer 16 is constructed by combining 7.0 grams Vulcan XC-72R carbon, 50 grams methyl ethyl ketone, 27.54 grams RTV 615 part A silicone, 3.24 grams RTV 615 part B silicone, and 10 grams silver flake. To prepare the solution, the carbon powder, methyl ethyl ketone, and part A silicone are mixed together. Once the solution is thoroughly mixed, the silver flake and part B silicone are added and the resulting solution is further mixed. Once the permeable conductive layer solution is applied to the dielectric core 12 (elastomeric layer of the sensor), the methyl ethyl ketone is allowed to evaporate and the silicone elastomer is cured by heating to a temperature between 150° F. and 250° F.

In addition to the permeable and conductive properties of the permeable conductive layer 16, in some embodiments of the organic chemical sensor 10, the permeable conductive layer 16 is secured to the elastomeric layer 12 in such a manner as to maintain the sensing area of the elastomeric layer to a constant size during the absorption of organic chemicals. An example of such a permeable conductive layer is a metal wire mesh screen.

The organic chemical sensor 10 further includes an electrically conductive layer 18 secured to the dielectric core 12. In one embodiment, the electrically conductive layer 18 is of the same construction as the permeable conductive layer 16 (e.g. metal wire mesh screen). In this embodiment, the electrically conductive layer 18 is also permeable to the organic chemical to be sensed which thus exposes the dielectric core 12 to the organic chemical from both sides. In other embodiments, the electrically conductive layer 18 is a solid layer, such as a sheet of metal foil, exemplarily copper.

The dielectric core 12 is secured to the electrically conductive layer 18 in such a manner that the area of the elastomeric layer is maintained at a constant area during the absorption of organic chemicals by the elastomeric layer. In one embodiment, this requires the selection of an electrically conductive layer 18 of a metal of sufficient thickness, as would be recognized by one of ordinary skill in the art, in order to provide the rigidity necessary to maintain the elastomeric layer at a fixed area.

It will further be recognized that due to the specific compositions of the dielectric core 12 and the electrically conductive layer 18, in some embodiments, an adhesive primer 20 is used between the dielectric core 12 and the electrically conductive layer 18 in order to secure the dielectric core 12 to the electrically conductive layer 18 in the desired manner. In alternative embodiments, the elastomer selected and the technique used to deposit and cure the elastomeric layer of the dielectric core 12 on the electrically conductive layer 18 can sufficiently secure the elastomeric layer to the electrically conductive layer 18. Such application techniques can include, but are not limited to, painting, casting, and screen printing. However, it will be recognized by one of ordinary skill in the art that the particular application method is to be selected based upon the actual compositions of the materials used.

In one exemplary embodiment, the organic chemical sensor is constructed with an active area of approximately 1 cm$^2$. In such an embodiment, the elastomeric layer is constructed in the manner disclosed above to have a thickness between 0.1 mm and 0.5 mm (0.004 in.-0.02 in.). In the same embodiment, the permeable conductive layer and the electrically conductive layer are constructed within the tolerances of the materials selected. Exemplarily, but not limiting, these conductive layers are approximately between 0.01 mm and 0.5 mm thick.

Figure 2:
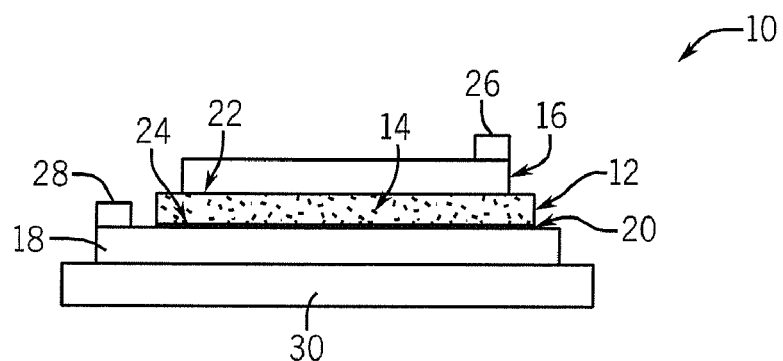
FIG. 2 is a side view of the organic chemical sensor of FIG. 1.

Specifically referring to FIG. 2, the organic chemical sensor 10 is constructed by securing an electrically conductive layer 18 to a first side 24 of the dielectric core 12 that includes the elastomeric layer and the high dielectric constant material 14. A permeable conductive layer 16 is secured to the elongated second side 22 of the dielectric core 12.

Electrical contacts 26 and 28 are respectively secured to the permeable conductive layer 16 and the electrically conductive layer 18. In a non-limiting exemplary embodiment, the electrical contacts 26 and 28 comprise electrically conductive silver paint.

In embodiments, the organic chemical sensor 10 further includes a support layer 30 that is secured to the electrically conductive layer 18. The support layer 30 provides rigidity to the sensor 10 that further aids in preventing any change in the area of the dielectric core 12 and permeable conductive layer 16. In one embodiment, the support layer 30 is constructed from a copper-clad polyimide available under the trademark Pyralux, available from DuPont. In such an embodiment, the polyimide provides the support layer for the sensor, while the copper-cladding can be etched to form the electrically conductive layer 18 of the organic chemical sensor 10. In one embodiment, the support layer 30 is constructed to have a Young's modulus of elasticity greater than 10,000 psi. Exemplarily, the support layer 30 is 1.25 mm thick.

It is to be noted that although the side view of the organic chemical sensor 10 shows the components of the sensor in relief, embodiments of the sensor 10 are constructed to be less than one millimeter in height and therefore the depiction in FIG. 2 (as well as the other side views) are merely descriptive of the components and are not intended to be representative of the scale or relative size of the components themselves of embodiments of the organic chemical sensor.

Figure 3:
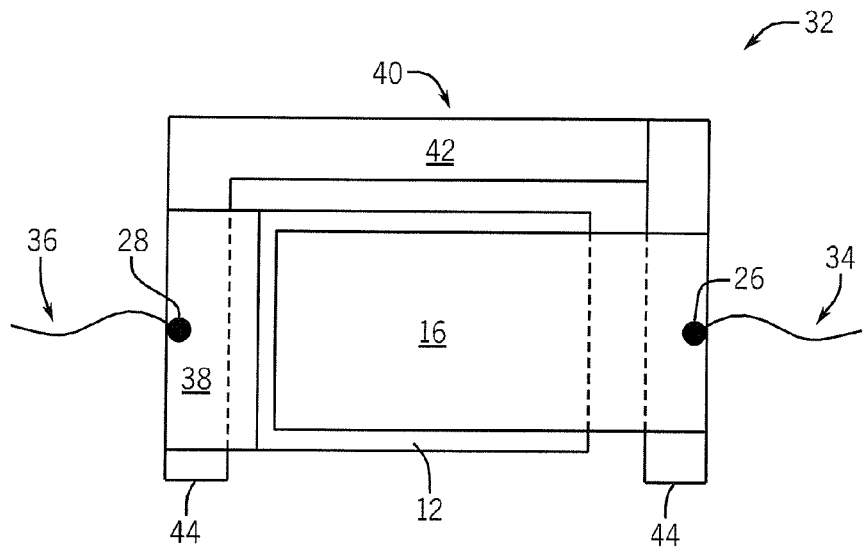
FIG. 3 is a top view of an alternative embodiment of an organic chemical sensor.
Figure 4:
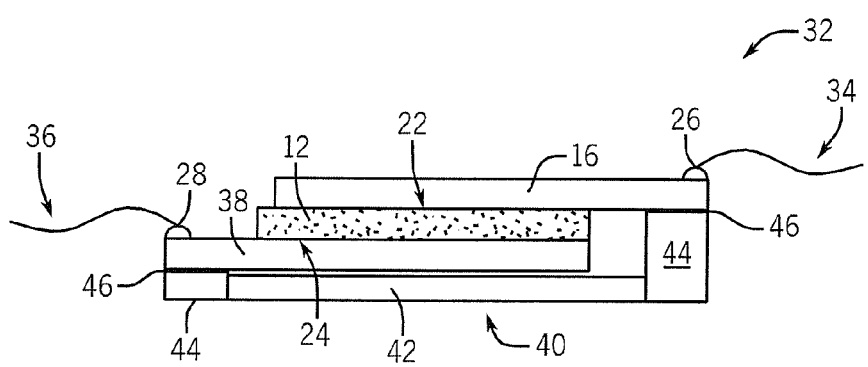
FIG. 4 is a side view of the organic chemical sensor of FIG. 3.

FIGS. 3 and 4 depict an alternative embodiment of an organic chemical sensor 32. It should be noted that in FIGS. 1-9, like reference numerals are used herein to describe like components in an effort to reduce redundancy in the description.

The organic chemical sensor 32 includes a dielectric core 12 that is secured to a permeable conductive layer 16 and an electrically conductive layer 38. As will be described in further detail herein, in the embodiment of the organic chemical sensor 32, the electrically conductive layer 38 is also permeable to the organic chemical to be sensed. Electrical contacts 26 and 28 are respectively connected to the permeable conductive layer 16 and the electrically conductive layer 38. In embodiments of the organic chemical sensor 32, the electrical contacts 26, 28 are soldered electrical connections between the respective conductive layers and the electrical leads 34 and 36. Electrical leads 34 and 36 are respectively connected to the electrical contacts 26, 28. The electrical leads 34, 36 are connected to capacitance sensing circuitry (not depicted) that will be described in further detail therein.

The support frame 40, in embodiments, is of a similar construction to that of the support layer 30 depicted in FIGS. 1 and 2. To these ends, the support frame 40 is constructed of a rigid material, such as a polyimide, glass reinforced epoxy board, or other material as would be recognized by one of ordinary skill in the art. In the embodiment of the support frame 40, the support frame 40 includes a cross member 42 from which two arms 44 extend. Opposing ends of the organic chemical sensor 32 are secured to the arms 44. The permeable conductive layer 16 is secured to one arm 44 with an adhesive 46 selected to bond the two structures. The electrically conductive layer 38 is similarly bonded to the other arm 44 with the adhesive 46. In embodiments wherein the electrically conductive layer 38 is also permeable to the organic chemical to be sensed, the dielectric core 12 is exposed to the organic chemical from both of the elongated sides 22, 24.

The organic chemical sensor 32 that includes the support frame 40 provides the advantage of rigidly supporting the organic chemical sensor 32, but also exposing both elongated sides 22, 24 of the dielectric core 12 to the organic chemical to be sensed.

Figure 5:
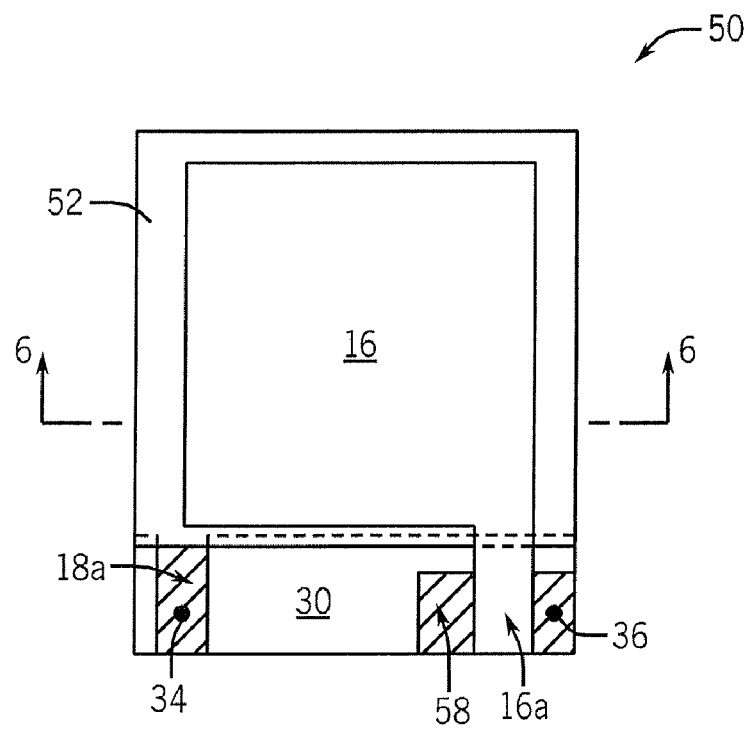
FIG. 5 is a top view of another embodiment of an organic chemical sensor.
Figure 6:
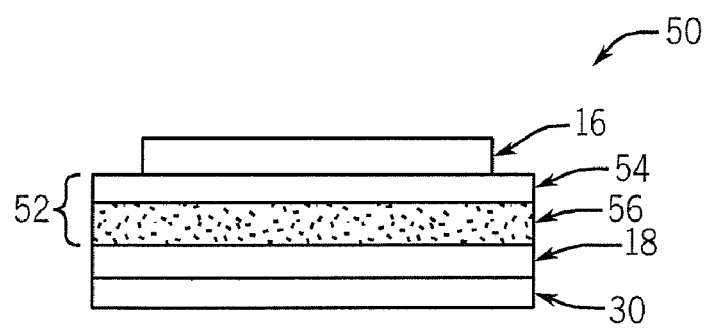
FIG. 6 is a sectional view of the organic chemical sensor of FIG. 5 along line 6-6.

FIGS. 5 and 6 depict an alternative embodiment of an organic chemical sensor 50. The organic chemical sensor 50 includes the electrically conductive layer 18 and the permeable conductive layer 16. The electrically conductive layer 18 is secured to the support layer 30. Electrical leads 34 and 36 extend respectively from electrical connections to the electrically conductive layer 18 and the permeable conductive layer 16.

Referring specifically to FIG. 6, which is a sectional view of the organic chemical sensor 50 taken along line 6-6, the dielectric core 52 of the organic chemical sensor 50 includes a separate elastomeric layer 54 of the organic chemical absorptive elastomeric material. The dielectric core 52 further includes a high dielectric constant insulative layer 56. In this embodiment, the high dielectric constant material is formed into a separate layer of the dielectric core 52 from the organic chemical absorptive elastomeric layer 54. The high dielectric constant insulative layer 56 is further constructed such as to provide electrical insulation between the elastomeric layer 54 and the electrically conductive layer 18, as this assures there are no electrical conductive paths through the dielectric core 52. In an embodiment, the high dielectric constant insulative layer 56 is a high dielectric constant material such as a thin barium titanate sheet which has been bonded to the electrically conductive layer 18.

Referring back to FIG. 5, and as disclosed previously above, the support layer 30 can be a copper-clad polyimide. In this exemplary embodiment, a portion of the copper-cladding layer has been etched away to form the electrically conductive layer 18 having a contact tab 18A at one end, and a contact area 58 for the tab 16A at one end of the permeable conductive layer 16. Electrical leads 34 and 36 are respectively soldered to the tab 18A and contact area 58.

Figure 7:
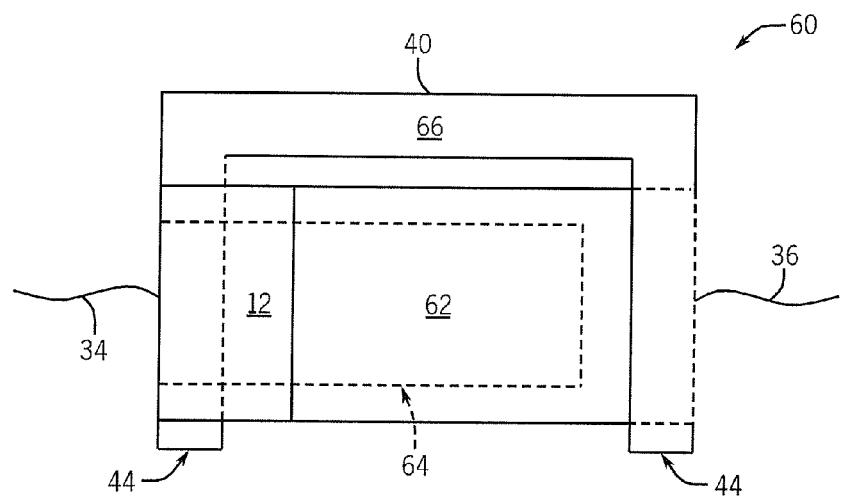
FIG. 7 is a top view of a still further embodiment of an organic chemical sensor.
Figure 8:
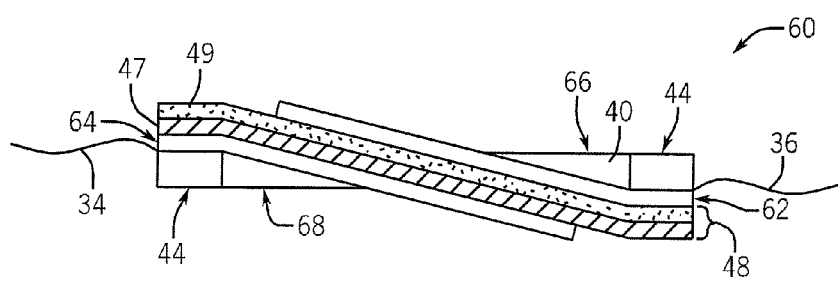
FIG. 8 is a side view of the organic chemical sensor of FIG. 7.

FIGS. 7 and 8 depict a still further embodiment of an organic chemical sensor 60. The organic chemical sensor 60 includes permeable conductive layer 62 and an electrically conductive layer 64 separated by a dielectric core 48. The organic chemical sensor 60 is structurally supported by a support frame 40 and the conductive layers 62, 64 and dielectric core 48 extend between the arms 44 of the support frame 40.

The organic chemical sensor 60 depicted in FIGS. 7 and 8 differs from the organic chemical sensor depicted in FIGS. 3 and 4 in that the sensor extends between a top surface 66 and a bottom surface 68 of the support frame 40. In the organic chemical sensor 60, electrically conductive layer 64 is secured to the top surface 66 of the support frame 40 and the permeable conductive layer 62 is secured to the bottom surface 68 of the support frame 40. The organic chemical sensor 60 provides the feature of additional rigidity from the support frame 40.

The dielectric core 48 is similar in construction to the dielectric core 52 depicted in FIGS. 5 and 6. However, the dielectric core 48 exemplifies an alternative dielectric core construction in that the dielectric core 48 includes a high dielectric constant elastomeric layer 49. The high dielectric constant elastomeric layer 49 may be constructed in the manner as disclosed above, exemplarily as a silicone elastomer with barium titanate particulates. The dielectric core 48 further includes an insulative support layer 47. The insulative support layer 47 runs the entire length of the organic chemical sensor 60 and thus provides additional support to the conductive layers 62, 64 and the high dielectric constant elastomeric layer 49. The insulative support layer 47 further assures that there is no electrical conductive path (e.g. pin hole) through the dielectric core 48 between the permeable conductive layer 62 and the electrically conductive layer 64. The insulative support layer 47 further helps to maintain a constant area of the dielectric core 48 during absorption of the organic chemical by the high dielectric constant elastomeric layer 49. In an exemplarily embodiment, the insulative support layer 47 is a polyimide film such as Upilex S available from UBE Industries, Ltd. In one embodiment, the insulative support layer 47 is positioned within the dielectric core 48 such that the insulative support layer 47 is secured to the electrically conductive layer 64 such that the insulative support layer 47 does not impede the absorption of the target organic chemical through the permeable conductive layer 62 and into the high dielectric constant elastomeric layer 49 of the dielectric core 48.

In an alternative embodiment (not depicted), two organic chemical sensors are connected in series in order to increase the active sensing area of the combined sensor. The organic chemical sensors of the combined sensor are connected in series by respectively connecting the electrically conductive layers and the permeable conductive layers of the organic chemical sensors to one another. Since the electrically conductive layers and the permeable conductive layers are connected in series, a capacitance meter, as will be disclosed in further detail herein, need only be connected to one of the electrically conductive layers and one of the permeable conductive layers of the combined organic chemical sensor. In a still further not depicted embodiment, the volumetric efficiency of the combined organic chemical sensor package is improved by using a single support layer to which both of the electrically conductive layers are secured. In an embodiment, one electrically conductive layer is secured to each of the opposing sides of a single support layer. In this embodiment, the single support layer provides rigidity and structure to both of the electrically conductive layers, which are connected in series to one another. This leaves the respective permeable conductive layers to be exposed to the environment for sensing the concentration of a targeted organic chemical.

Figure 9:
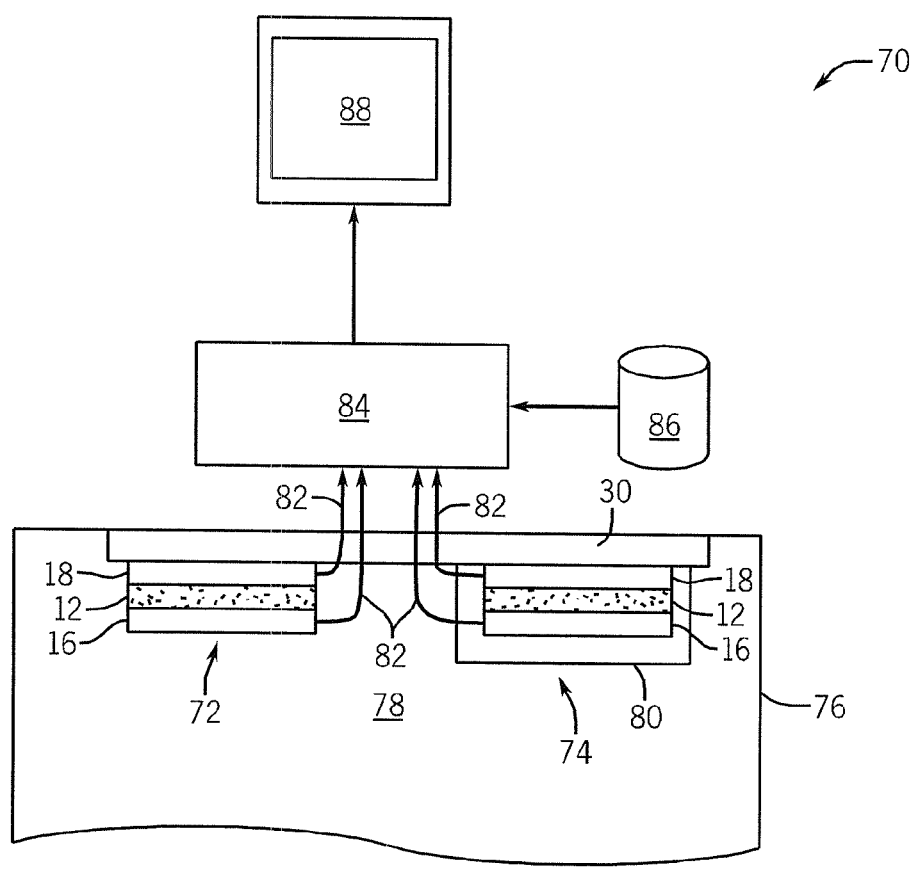
FIG. 9 is a schematic diagram of an embodiment of a system for monitoring the concentration of an organic chemical.

FIG. 9 is a system diagram depicting the implementation of an embodiment of a system 70 for sensing a concentration of an organic chemical vapor with temperature compensation control. The system 70 includes a first organic chemical sensor 72 and a second organic chemical sensor 74 of an identical construction. The organic chemical sensors 72, 74 include at least an electrically conductive layer 18, a permeable conductive layer 16 and a dielectric core 12. The organic chemical sensors 72, 74 are secured to a support layer 30. In an embodiment, the support layer 30 may be a single support layer 30 that supports both the first organic chemical sensor 72 and the second organic chemical sensor 74. Alternatively, separate support layers may be used for each of the organic chemical sensors. The first organic chemical sensor 72 and the second organic chemical sensor 74 are disposed within an environment 76 to be tested that includes organic chemical vapor 78. The second organic chemical sensor 74 is surrounded by a hermetic seal 80, exemplarily provided by a cover or fluid impervious coating. The hermetic seal 80 prevents the exposure of the second organic chemical sensor 74 to the organic chemical vapor 78. By providing the second organic chemical sensor 74 independent of exposure to the organic chemical vapor, the capacitance of the second organic chemical sensor 74 can be used for temperature compensation control as will be disclosed in further detail herein.

Electrical leads 82 extend from the electrically conductive layer 18 and the permeable conductive layer 16 of both the first organic chemical sensor 72 and the second organic chemical sensor 74. The electrical leads 82 are provided to a digital signal processor 84. The digital signal processor 84 executes computer readable code stored on a non-transient computer readable medium 86. The execution of the computer readable code by the digital signal processor 84 causes the digital signal processor 84 to operate in such a manner as to perform the functions as disclosed herein. It is to be recognized by one of ordinary skill in the art that alternatively, the non-transient computer readable medium 86 may be an integral part of the digital signal processor, or may be any other form of non-volatile computer memory.

The digital signal processor 84 receives the electrical signals from the electrical leads 82. It is to be understood that while not depicted, the electrical leads 82 may first provide the electrical signals to some form of signal processing, such as filtering or analog to digital conversion (ADC) before providing the signals to the digital signal processor 84. The digital signal processor uses the signals from the electrical leads 82 in order to measure a change in capacitance across the first organic chemical sensor 72 and the second organic chemical sensor 74. The change in the capacitance across the first organic chemical sensor is indicative of the concentration of the organic chemical vapor 78 within the environment 76 for the reasons disclosed above.

However, the dielectric core 12 of the organic chemical sensors 72, 74 are sensitive to fluctuations in temperature. Therefore, the signals from the electrical leads 82 from the second organic chemical sensor 74 that is hermetically sealed provide an indication of the changes in capacitance of the organic chemical sensors 72, 74 independent from the concentration of organic chemical vapor 78 in the environment 76. Therefore, the digital signal processor 84 uses these signals from the second organic chemical sensor 74 to derive any changes in capacitance of the second organic chemical sensor 74 due to temperature fluctuations in the environment 76.

The digital signal processor 84 uses the temperature compensated changes in capacitance of the first organic chemical sensor 72 to derive an indication of the concentration of the organic chemical vapor 78 in the environment 76. In one embodiment, the computer readable medium 86 comprises a lookup table that relates the changes in temperature-adjusted capacitance to organic chemical vapor concentration. However, a person of ordinary skill in the art will recognize that there are other manners of relating the capacitance to the organic chemical concentration that fall within the scope of the present disclosure.

The digital signal processor 84 further operates a graphical display 88 in order to present an indication of the identified organic chemical concentration. The presentation of the identified organic chemical concentration may be in the form of an actual measurement such as a percentage or parts per million. Alternatively, the graphical display 88 may be operated to produce an alarm or other indication such as a graphical of textual warning if the identified organic chemical concentration is above one or more predetermined concentration thresholds.

It is understood that while the embodiment of the system 70 depicted in FIG. 9 depicts the use of a digital signal processor 84, similar implementation may be performed using analog circuitry of which the suitable design and similar function would be recognized by one of ordinary skill in the art.

FIG. 10 is a graph that depicts the improved sensitivity obtained in the organic chemical sensors of the present disclosure. The graph of FIG. 10 shows the percentage of change in capacitance measured across embodiments of the organic chemical sensor when exposed to gasoline saturated air. The four exemplary organic chemical sensors used in achieving the results depicted in the graph of FIG. 10 each comprise various concentrations of barium titanate particulate material. Reference numeral 90 identifies a graph representing the change in capacitance in a sensor that includes no barium titanate in the dielectric core. Reference 92 identifies a graph of the change in capacitance in a sensor that comprised 70% by weight barium titanate in the dielectric core. Reference 94 is a graph that represents a change in capacitance measured by a sensor that comprises 75% by weight barium titanate in the dielectric core. Reference 96 identifies a graph of the change in capacitance measured by a sensor that comprises 80% by weight barium titanate in the dielectric core. In the tests shown in the graph of FIG. 10, the barium titanate used in the sensors has a dielectric constant of 2700.

A number of features or characteristics of the organic chemical sensors as disclosed herein are highlighted by the graph in FIG. 10. First, as the percentage by weight of barium titanate in the dielectric core increases, the percentage change in capacitance of the sensor increases when exposed to the same concentration of an organic chemical vapor. This highlights the increase in sensitivity that is achieved with the addition of the high dielectric constant material to the dielectric core of the sensor. However, it was a surprising result to find that as much percentage change in sensitivity gain was achieved by the increase from 70% by weight barium titanate to 80% by weight barium titanate as was achieved by the increase from no barium titanate to 70% by weight barium titanate. These results indicate that the increase in sensitivity from the use of additional barium titanate in the dielectric core is not linear to the concentration of the barium titanate in the dielectric core.

Additionally, while the various concentrations produce increasing percentage changes in steady state capacitance, various concentrations produced differing results in instantaneous capacitance change as well. In particular, the increase between the instantaneous capacitance change achieved between the 70% barium titanate sensor 92 and the 75% barium titanate sensor 94 is to be noted. Additionally, the instantaneous capacitance changes overall provide a greater distinction between the detected capacitance changes across barium titanate concentration percentages. Exemplary, while a comparison of steady state capacitance changes between the no barium titanate sensor 90 and the 80% barium titanate sensor 96 indicated a 66.3% increase in steady state sensitivity (100(25.87−15.56)/15.56=66.3%) when instantaneous capacitance changes (represented by the first measured % change in capacitance e.g. 1 minute) are compared, the 80% barium titanate sensor 96 provides an instantaneous sensitivity increase of 301.6% (100(14.86−3.70)/3.70=301.6%). Therefore, it was surprising to find that while the embodiments of the sensor as disclosed herein provided increases in steady state sensitivity, the sensors produce significantly greater increases in instantaneous sensitivity.

Still referring to FIG. 10, reference numeral 100 identifies another surprising feature that was discovered with the 80% barium titanate sensor embodiment 96. In the graph of FIG. 10, each of the exemplary sensors were returned to fresh air at a time of 60 minutes. Reference numeral 98 highlights that the sensor embodiment with no, 70%, and 75% barium titanate (90, 92, 94) all quickly return to within 5% of the original sensor capacitance prior to gasoline exposure after 15 minutes exposure to fresh air. The changing capacitance of these three sensors follows a natural log pattern and solely approaches the pre-exposure capacitance (0% change). To contrary, the 80% barium titanate sensor 96 overshoots the original capacitance at reference numeral 100. In an experimental result, the measured capacitance returns to the original capacitance over time. This capacitance overshoot can provide technical advantages in embodiments as disclosed in the specification in that the positive change in capacitance embodied in the overshoot can be repeatedly detected.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A capacitive organic chemical sensor comprising:
   a dielectric core that comprises an elastomeric layer and high dielectric constant particles of a complex metal oxide comprising titanium oxide dispersed within the elastomeric layer, the dielectric core having a first side and a second side, and the elastomeric layer capable of absorbing an organic chemical to be sensed;

an electrically conductive layer secured to the first side of the dielectric core;

a permeable conductive layer secured to the second side of the dielectric core, the permeable conductive layer being electrically conductive and permeable to the organic chemical; and a first electrical contact secured to the electrically conductive layer and a second electrical contact secured to the permeable conductive layer;

wherein absorption of the organic chemical by the elastomer causes a decrease in a capacitance between the electrically conductive layer and the permeable conductive layer.

2. The capacitive organic chemical sensor of claim 1, further comprising a support layer secured to the electrically conductive layer, wherein the support layer provides physical support to the organic chemical sensor.

3. The capacitive organic chemical sensor of claim 2, wherein the support layer is polyimide.

4. The capacitive organic chemical sensor of claim 1, further comprising an adhesive primer layer between the electrically conductive layer and the dielectric core, the adhesive primer layer secures the electrically conductive layer to the first side of the dielectric core.

5. The capacitive organic chemical sensor of claim 1, wherein the high dielectric constant particles have a dielectric constant greater than 1000.

6. The capacitive organic chemical sensor of claim 1, wherein the complex metal oxide is barium titanate, strontium titanate, or barium strontium titanate.

7. The capacitive organic chemical sensor of claim 6, wherein the high dielectric constant particles are barium titanate.

8. The capacitive organic chemical sensor of claim 7 wherein the dielectric core comprises between 70 and 80 percent by weight barium titanate.

9. The capacitive organic chemical sensor of claim 1, wherein the elastomer is silicone, polyurethane, or an ethylene propylene rubber.

10. A capacitive organic chemical sensing system, comprising:

a dielectric core that comprises an elastomeric layer and high dielectric constant particles of a complex metal oxide comprising titanium oxide dispersed throughout the elastomeric layer, the elastomeric layer having an elongated first surface and an elongated second surface and capable of absorbing an organic chemical to be sensed;

an electrically conductive layer secured to the elongated first surface of the elastomeric layer, wherein the electrically conductive layer fixes an area of the elongated first surface of the elastomeric layer so that the area remains constant upon absorption of the organic chemical by the elastomeric layer;

a permeable conductive layer secured to the elongated second surface of the elastomeric layer, the permeable conductive layer being electrically conductive and permeable to the organic chemical; and a first electrical contact secured to the electrically conductive layer and a second electrical contact secured to the permeable conductive layer;

wherein absorption of the organic chemical by the elastomeric layer causes a decrease in the capacitance between the electrically conductive layer and the permeable conductive layer as absorption of the organic chemical by the elastomeric layer decreases a dielectric constant of the elastomeric layer and increases a volume of the elastomeric layer thus increasing a distance between the electrically conductive layer and the permeable conductive layer as the area of the first surface remains constant.

11. The organic chemical sensing system of claim 10, further comprising:

a first lead extending from the first electrical contact;

a second lead extending from the second electric contact;

a controller electrically connected to the first lead and the second lead, the controller measures a capacitance between the electrically conductive layer and the permeable conductive layer.

12. The organic chemical sensing system of claim 11, wherein the controller further derives a concentration of the organic chemical to be sensed from a measured decrease in capacitance between the electrically conductive layer and the permeable conductive layer.

13. The organic chemical sensing system of claim 12, further comprising a graphical display that is operated by the controller to present an indication of the derived concentration of the organic chemical.

14. The organic chemical sensing system of claim 10, wherein an area of overlap between the electrically conductive layer and the permeable conductive layer is smaller than an area of the elastomeric layer.

15. The organic chemical sensing system of claim 10, wherein the permeable conductive layer maintains an area of the elongated second surface of the elastomeric layer at a constant area when the organic chemical is absorbed by the elastomeric layer.

16. The organic chemical sensing system of claim 10 further comprising an insulative support layer secured between the elongated first surface of the elastomeric layer and the electrically conductive layer.

17. The capacitive organic chemical sensing system of claim 10 wherein the complex metal oxide is barium titanate, strontium titanate, or barium strontium titanate.

18. The capacitive organic chemical sensor of claim 10, wherein the elastomer is silicone, polyurethane, or ethylene propylene rubber.

19. The capacitive organic chemical sensor of claim 10, which further comprises a second capacitive organic chemical sensor of the same structure as recited in claim 10, enclosed in a hermetically sealed container, wherein the second capacitive organic chemical sensor serves as a reference sensor to correct capacitance measurements of the first capacitive organic chemical sensor due to the temperature fluctuations in the environment.

20. A capacitive organic chemical sensor comprising:

a dielectric core comprising an elastomeric layer as a first side and a high dielectric constant layer comprising a complex metal oxide comprising titanium oxide as a second side, the elastomeric layer secured to the high dielectric constant layer, wherein the elastomeric layer absorbs an organic chemical to be sensed;

a permeable conductive layer secured to the elastomeric layer on the first side of the dielectric core, the permeable conductive layer being electrically conductive and permeable to the organic chemical to be sensed;

an electrically conductive layer secured to the high dielectric constant layer on the second side of the dielectric core wherein the high dielectric constant layer electrically insulates against electrical discharge between the permeable conductive layer and the electrically conductive layer; and a first electrical contact secured to the electrically conductive layer and a second electrical contact secured to the permeable conductive layer;

wherein absorption of the organic chemical to be sensed by the elastomeric layer causes a decrease in a capacitance between the electrically conductive layer and the permeable conductive layer.

21. The capacitive organic chemical sensor of claim 20 wherein the complex metal oxide is barium titanate, strontium titanate, or barium strontium titanate.

22. The capacitive organic chemical sensor of claim 20, wherein the elastomer is silicone, polyurethane, or ethylene propylene rubber.

* * * * *